United States Patent
Edvardsson et al.

(10) Patent No.: US 8,178,035 B2
(45) Date of Patent: *May 15, 2012

(54) APPARATUS AND METHOD FOR FORMING AIR-LAID ABSORBENT CORES

(75) Inventors: Gunnar Edvardsson, Bohus Björkö (SE); Henrik Carlén, Västra Frölunda (SE)

(73) Assignee: SCA Hygiene Products AB, Gothenburg (SE)

( * ) Notice: Subject to any disclaimer, the term of this patent is extended or adjusted under 35 U.S.C. 154(b) by 204 days.

This patent is subject to a terminal disclaimer.

(21) Appl. No.: 12/373,786

(22) PCT Filed: Jul. 20, 2006

(86) PCT No.: PCT/SE2006/050267
§ 371 (c)(1),
(2), (4) Date: Jan. 14, 2009

(87) PCT Pub. No.: WO2008/010752
PCT Pub. Date: Jan. 24, 2008

(65) Prior Publication Data
US 2009/0212468 A1 Aug. 27, 2009

(51) Int. Cl.
*B27N 3/08* (2006.01)
(52) U.S. Cl. ........ 264/517; 264/299; 264/310; 264/319; 425/436 R
(58) Field of Classification Search .................. None
See application file for complete search history.

(56) References Cited

U.S. PATENT DOCUMENTS

| | | | |
|---|---|---|---|
| 3,973,291 A | 8/1976 | Kolbach | |
| 4,388,056 A | 6/1983 | Lee et al. | |
| 4,598,441 A * | 7/1986 | Stemmler | 19/145 |
| 5,030,314 A | 7/1991 | Lang | |
| 5,064,484 A * | 11/1991 | Craig et al. | 156/62.6 |
| 5,575,874 A | 11/1996 | Griesbach, III et al. | |

(Continued)

FOREIGN PATENT DOCUMENTS
DE  1 510 427 B  10/1970
(Continued)

OTHER PUBLICATIONS
PCT/ISA/210, PCT/SE2006/050267 Mar. 5, 2007.
(Continued)

*Primary Examiner* — Monica A Huson
(74) *Attorney, Agent, or Firm* — Buchanan Ingersoll & Rooney PC

(57) ABSTRACT

An apparatus for forming air-laid absorbent cores, having a first and second mat-forming wheel, means for transferring a core element on the first mat-forming wheel onto a core element on the second mat-forming wheel while the latter core element still is maintained in its mold. The apparatus has means for applying a protective layer to the bottom of each mold of the second mat-forming wheel, means for applying a web of casing material on the peripheral surface of the first mat-forming wheel, means for guiding said web of casing material onto the periphery of the second mat-forming wheel, and means for changing the synchronization of the mat-forming wheels in order to control the time at which the leading edge of a mold on one of the mat-forming wheels passes the nip. A method of producing cores with different sizes without change of molds.

12 Claims, 2 Drawing Sheets

U.S. PATENT DOCUMENTS

| | | |
|---|---|---|
| 6,330,735 B1 | 12/2001 | Hahn et al. |
| 6,652,798 B1 | 11/2003 | Edvardsson |
| 6,811,642 B2 | 11/2004 | Ochi |
| 2002/0056516 A1 | 5/2002 | Ochi |
| 2005/0109442 A1 | 5/2005 | Neubauer et al. |
| 2006/0021695 A1 | 2/2006 | Blessing et al. |
| 2006/0024433 A1 | 2/2006 | Blessing et al. |
| 2006/0048880 A1 | 3/2006 | Blessing et al. |

FOREIGN PATENT DOCUMENTS

| | | |
|---|---|---|
| DE | 43 35 919 A1 | 4/1995 |
| EP | 0 292 624 A1 | 11/1988 |
| EP | 0 958 801 B1 | 11/1999 |
| EP | 1 082 081 B1 | 3/2001 |
| EP | 1 621 167 A1 | 2/2006 |
| FR | 2 690 843 A1 | 11/1993 |
| JP | 63-139547 A | 6/1988 |
| JP | 2-107250 A | 4/1990 |
| JP | 7-150456 A | 6/1995 |
| JP | 11-318977 A | 11/1999 |
| JP | 2002-516191 A | 6/2002 |
| JP | 2006-016727 A | 1/2006 |
| WO | WO 99/60964 A1 | 12/1999 |
| WO | WO 2005/072671 A1 | 8/2005 |

OTHER PUBLICATIONS

PCT/ISA/237, PCT/SE2006/050267 Mar. 5, 2007.
U.S. Appl. No. 12/373,780, Edvardsson, "An Apparatus and Method for Forming Air-Laid Absorbent Cores", filed Jan. 14, 2009.
U.S. Appl. No. 12/373,728, Edvardsson et al., "Mat-Forming Wheel", filed Jan. 14, 2009.
U.S. Appl. No. 12/373,729, Edvardsson, "An Apparatus and Method for Forming Air-Laid Absorbent Cores", filed Jan. 14, 2009.
Office Action issued on Aug. 16, 2011, in corresponding Japanese Patent Application No. 2009-520700.

* cited by examiner

APPARATUS AND METHOD FOR FORMING AIR-LAID ABSORBENT CORES

TECHNICAL FIELD

The present disclosure relates to an apparatus for forming air-laid absorbent cores, comprising a first and second mat-forming wheel, each of the mat-forming wheels having a series of moulds along its peripheral surface, air-laying means for supplying air-entrained fibrous material to the moulds on each mat-forming wheel, suction means maintaining the formed core elements in the respective moulds during a part of the path of the moulds on the respective mat-forming wheel and means for transferring a core element on the first mat-forming wheel onto the peripheral surface on the second mat-forming wheel while the latter core element still is maintained in its mould, and a method using such an apparatus.

BACKGROUND

Apparatuses of the kind referred to above are used to produce multi-layered absorbent cores, at least one of the layers containing discrete particles of a highly absorbent material, preferably a so called superabsorbent material (SAP), which can absorb liquid in an amount several times it own weight. The fibres in the layers are preferably cellulosic and produced by defibration of pulp. Additionally, other types of fibres can be added. The fibres in the different layers can be the same or different.

Apparatuses according to the present disclosure are to be disposed in a manufacturing line for producing absorbent articles, such as disposable diapers, sanitary napkins, incontinence protectors and the like sanitary articles. It is therefore important that such apparatuses do not occupy a lot of space, especially in the length direction of such a production line. Nowadays, the production rate of such a production rate is high, approximately 600 cores per minute, and the present disclosure aims to allow even higher production rates. In such high speeds the centrifugal forces acting on the discrete particles in formed core elements are quite high and there is a problem of preventing these particles from falling out of such core elements. Apart from the cost consequence of losing relative expensive particle material, there is a risk that the lost particles will fall on components or equipment in the production line an adversely influence the functions thereof. Lost particles must therefore somehow be taken care of. There is therefore a need to keep such losses of particles as low as possible.

Another problem is to ensure that the core elements formed on the respective mat-forming wheel of an apparatus of the kind described in the introduction are superposed on each other in the desired mutual relationship. If, for example, the leading edges of the superposed core elements are to be aligned with each other, a misalignment will visually be very apparent and will also adversely influence the function of the produced article. For example, if the produced article contains openings or the like in the superposed cores which should coincide or have a determined relationship relative each other in the superposed position of the core elements, a misalignment of those openings will have a detrimental effect on the functioning of the produced article.

A further problem with an apparatus according to the introduction is that there is a risk that the discrete particles air-laid onto a mould will damage the mould or obstruct or clog some of the openings in the mould. Such obstructions or clogging leads to an uneven distribution of air-laid material in the mould and will consequently adversely affect the absorptive properties of the produced article.

In EP-B1-O 958 801 is shown an apparatus, in which a web of tissue is wound on a mat-forming wheel and drawn against the walls of the moulds on the peripheral surface of the wheel. Thereafter, a layer of discrete particles is air-laid in the mould and air-entrained fibres are drawn into this layer of discrete particles to mix with the discrete particles. In FIG. 3 of this document, such an apparatus having two mat-forming wheels is disclosed. The air-laid bodies are delivered from each mat-forming wheel attached to the webs of tissue and the two webs of tissue together with the attached bodies are then superposed on each other. The bodies attached to the webs travel a rather long distance without suction means influencing the bodies thereon and there is a great risk that particles will fall out of the bodies during this travel. Moreover, with such a construction it seems hard to obtain a great accuracy of the relative positions of the bodies attached to the webs when superposed to each other.

In EP-B1-I 082 081 an apparatus according to the preamble of Claim 1 is disclosed. In such an apparatus, only fibrous material is air-laid in the moulds on the first mat-forming wheel for forming a body on which a second body composed of a mixture of fibrous material and discrete particles of SAP is transferred from the second mat-forming wheel while the first body is still in its mould. A third layer of fibrous material is then air-laid over the composite of the first two bodies. During the transfer of the second body onto the first body, a part of the second body is always in the free air exposing both its sides thereto. There is thus a great risk that SAP-particles will fall out of these exposed parts of the second body, especially if the concentration thereof is high and the speed of the mat-forming wheels are high. After transfer of the second body onto the first body, the third layer air-laid thereon will prevent the SAP-particles in the second body from falling out. Although the accuracy of the positions of the superposed bodies is improved due to the first body being maintained in its mould during the transfer of the second body thereon, the second body has to move in free air before being superposed onto the first body, a fact that reduces accuracy. Moreover, in the second mat-forming wheel there are no means for preventing discrete particles air-laid in the moulds to obstruct or clog the openings in the bottoms of these moulds.

Sanitary absorbent articles, such as diapers, are often provided in different sizes. When such different sizes of cores for the "same" absorbent article are to be produced on the same apparatus, like the apparatus described in the introduction, the moulds on the mat-forming wheels have to be changed. This is a time-consuming operation, which also involve storage of the different moulds not used for the size in question and which reduce the cost-efficiency of the manufacturing process, especially for small product series.

OBJECTS AND SUMMARY

It is an objective of the present disclosure to in an apparatus according to the introduction improve the accuracy of the transfer of a core element onto another, prevent air-laid discrete particles from damaging and/or clogging the moulds and prevent excessive losses of discrete particles from formed core elements. Moreover, it is an objective of the present disclosure to reduce the need for changing moulds when different sizes of the same product are to be produced. Another objective is to change the properties of the core by simple means. It is also an objective of the present disclosure to accomplish this without significantly increase the space required for the apparatus in a production line for the manufacturing of sanitary absorbent articles.

These objectives are accomplished by an apparatus for forming air-laid absorbent cores, comprising a first and second mat-forming wheel, each of the mat-forming wheels having a series of moulds along their peripheral surface, air-laying means for supplying air-entrained fibrous material to the moulds on each mat-forming wheel, suction means maintaining the formed core elements in the respective moulds during a part of the path of the moulds on the respective mat-forming wheel and means for transferring a core element on the first mat-forming wheel onto the peripheral surface of the second mat-forming wheel while the core element on the second mat-forming wheel still is maintained in its mould, characterized by means for applying a web of casing material on the peripheral surface of the first mat-forming wheel, whereby suction means inside the first mat-forming wheel will draw the material in the web to abutment against the bottom of a mould passing said suction means, means for guiding said web of casing material onto the periphery of the second mat-forming wheel after having passed the nip between the first and second mat-forming wheel, and means for changing the synchronization of the mat-forming wheels in order to control the time at which the leading edge of a mould on one of the mat-forming wheels passes the nip in relation to when the leading edge of a mould on the other mat-forming wheel passes the nip.

In a preferred embodiment at least the air-laying means associated with the second mat-forming wheel and preferably both the first and second mat-forming wheel include means for supplying a mixture of air-entrained fibrous material and discrete particles and means for applying a web of nonwoven to the peripheral surface of each mat-forming wheel. The moulds can have different sizes, at least in the circumferential direction of the mat-forming wheels, and the moulds on the first mat-forming wheel is larger than the moulds on the second mat-forming wheel.

The disclosure also relates to a method of forming air-laid absorbent cores, comprising the steps of: forming first and second core elements by air-laying of air-entrained fibrous material to moulds on a first and second mat-forming wheel, each of said mat-forming wheels having a series of moulds along their peripheral surface, wherein each mould on the first and second mat-forming wheel has a leading edge and a trailing edge; characterized by applying a web of nonwoven to the peripheral surface of the first mat-forming wheel before air-laying of a mixture of air-entrained fibrous material and optionally discrete particles in the mould; transferring said web of nonwoven material to the periphery of the second mat-forming wheel after having passed the nip between the first and second mat-forming wheel, whereby first core elements is transferred together with the web onto the periphery of the second mat-forming wheel; controlling the time at which the leading edge of a mould on one of the mat-forming wheels passes the nip in relation to when the leading edge of a mould on the other mat-forming wheel passes the nip; controlling the time at which the leading edge of a mould on one of the mat-forming wheels passes the nip in relation to when the leading edge of a mould on the other mat-forming wheel passes the nip in dependence of desired relative positions of the first and second core elements on the peripheral surface of the second mat-forming wheel; and transfer the core elements from the second mat-forming wheel to other components in a production line for the manufacturing of sanitary absorbent articles.

In the preferred embodiment the leading edge of the moulds on the first mat-forming wheel passes the nip formed between the first and second mat-forming wheels before the leading edge of the moulds on the second mat-forming wheel, and the trailing edge of the moulds on the first mat-forming wheel passes the nip formed between the first and second mat-forming wheels before the trailing edge of the moulds on the second mat-forming wheel. By such an arrangement the core elements are superposed on each other In another preferred embodiment the leading edge and trailing edge of the moulds on the first mat-forming wheel passes the nip formed between the first and second mat-forming wheels before the leading edge of the moulds on the second mat-forming wheel.

In both embodiments a mixture of air-entrained fibrous material and discrete particles is preferably supplied to both the first and second mat-forming wheel and a web of non-woven is applied to the peripheral surface of both the first and second mat-forming wheel. A web of casing material is advantageously applied to each of the first and second mat-forming wheels and an adhesive coating is applied on the side of at least one of said webs distal from the bottom of the moulds.

BRIEF DESCRIPTION OF THE DRAWINGS

The disclosure will now be described with reference to the enclosed Figures, which are for the purpose of illustration of various non-limiting embodiments of the disclosure, of which.

DESCRIPTION OF EMBODIMENTS

Figure 1:
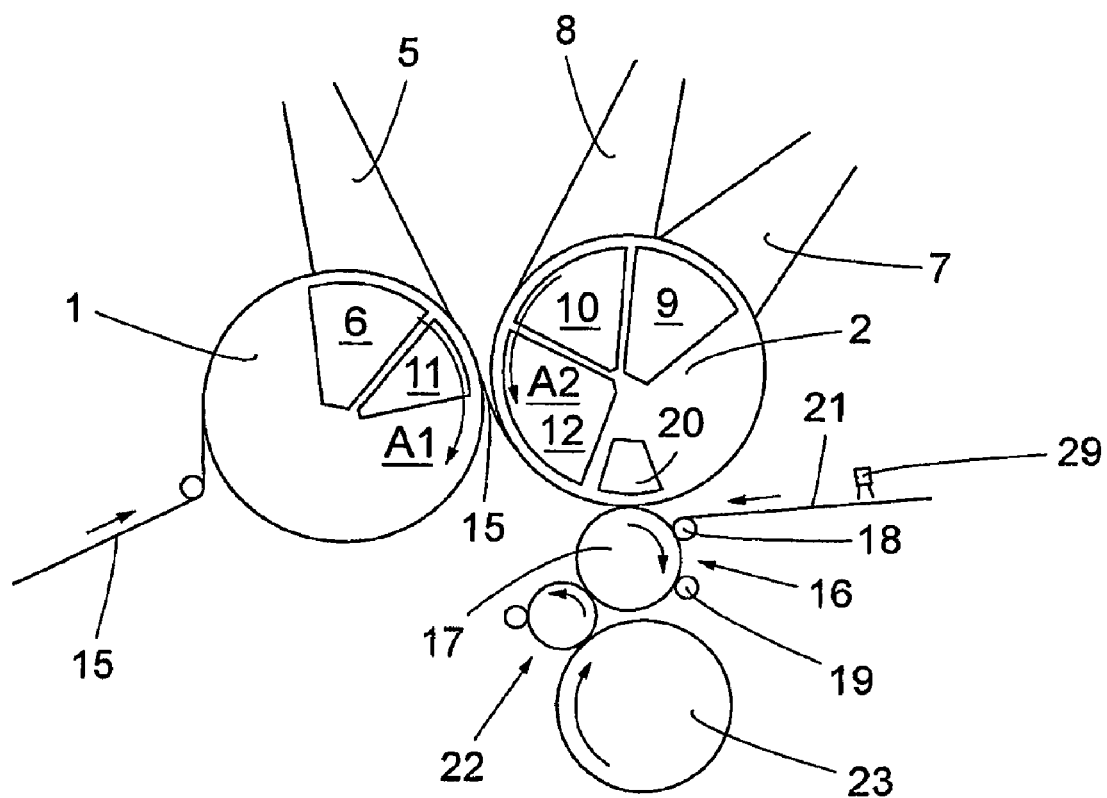
FIG. 1 schematically shows a side view of an apparatus for forming air-laid absorbent cores according to a preferred embodiment of the disclosure, and FIG. 2 schematically shows a sectional side view of a part of the apparatus in FIG. 1 in a larger scale.
Figure 2:
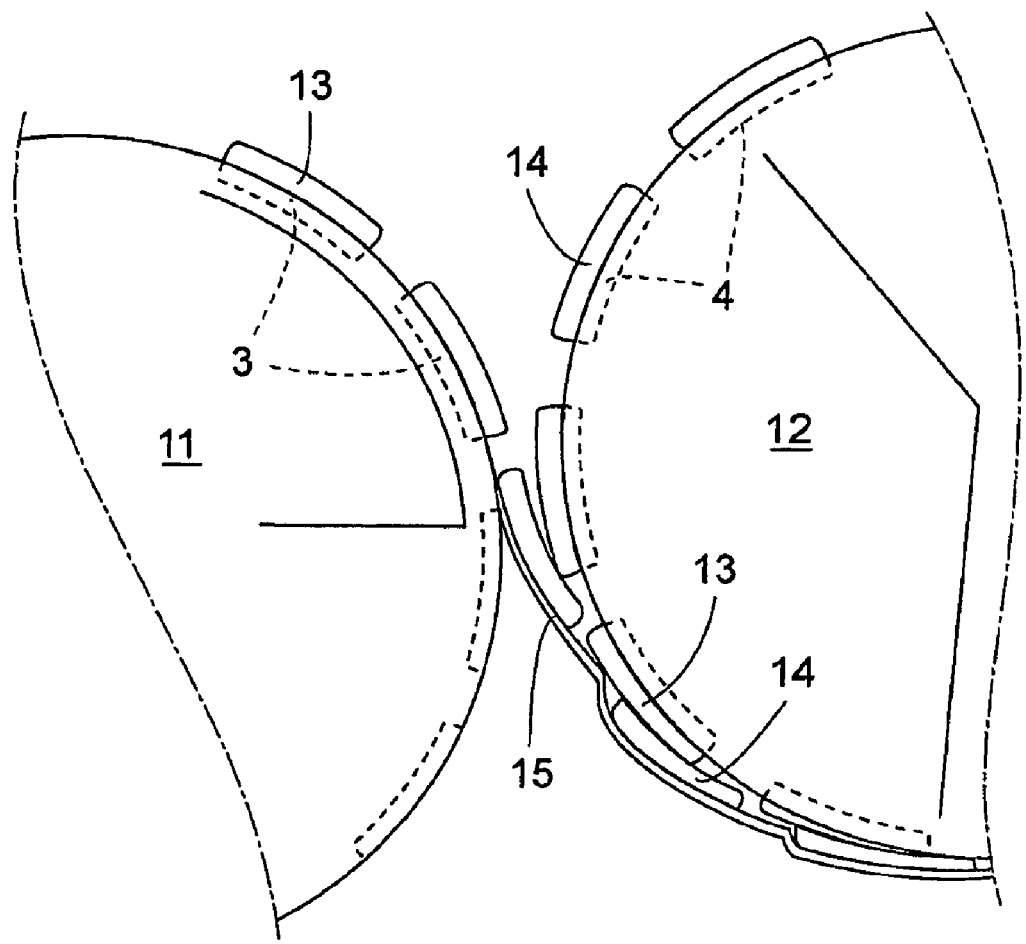

In FIGS. 1 and 2, a first preferred embodiment of an apparatus for forming air-laid absorbent cores is schematically disclosed. The apparatus includes two formation drums or mat-forming wheels, a first wheel 1 and a second wheel 2, each having a series of moulds 3 and 4 (see FIG. 2 in which the moulds are shown by interrupted lines), respectively, on their peripheral surfaces. The mould bottom or screen can be made of wire mesh or perforated steel sheet. Associated to the peripheral surfaces of the two mat-forming wheels 1 is a formation chamber or hood 5. Opposite this hood a suction box is disposed inside the wheel 1 in order to drawn air-entrained pulp or a mixture of pulp and SAP-particles into a mould 3 passing between hood 5 and box 6. Two hoods 7,8 with co-operating suction boxes 9,10 are associated with the second mat-forming wheel 2.

The apparatus also comprises a mill, for example a hammer mill, for defibration of pulp, pipes used for fibre or fibre/SAP transport, and a fan for the transport of fibre or fibre/SAP to the respective hood 5, 7 and 8. These components are conventional and well know to one skilled in the art and will not be further described. For the understanding of the present disclosure it is enough to say that a homogenous mixture of air fibres and possible SAP-particles are present in the hoods 5,7 and 8 when the apparatus is in use. Each hood 5,7 and 8 is cooperating with a separate suction box 6,9 and 10, respectively, which is stationary and located in the interior of the respective mat-forming wheel, i.e suction box 6 is disposed inside the first wheel 1 and suction boxes 9,10 are disposed inside the second wheel 2. When the moulds on the peripheral surface of each wheel pass between a hood and its associated suction box during the rotation of the wheel, the air-entrained material in the hood will be drawn into the mould and deposited therein. In the mat-forming wheels 1,2, suction boxes 11 and 12, respectively, are present for maintaining the core elements formed in the moulds in the their respective mould and for maintaining the shape of the formed core elements.

The mat-forming wheels 1,2 are disposed side-by-side, the nip between them being dimensioned to be at least 6 mm. The term "nip" denotes the point at which the peripheries of the wheels 1,2 are closest to each other.

In the apparatus according to FIGS. 1 and 2, the first core element 13 (see FIG. 2) formed on the first mat-forming wheel 1 is transferred onto the first core element 14 formed on the second mat-forming wheel 2 and held thereon partly by the suction created by suction box 12 and a partly by web 15 of nonwoven material, as will be described in detail below, until the composite core comprising core elements 13,14 is delivered to a compression device 16 consisting of two rollers 18,19 co-operating with a transfer roller 17.

Inside the wheel 2 a blowing box 20 in which an overpressure is created blows the core element 14 out of its mould and onto the transfer roller 17. Before the core on the transfer roller 17 enters between the first roller 18 of the compression device 16, a second web 21 of nonwoven or tissue is applied to the outer side of the composite core 13,14, i.e. the side opposite to which the first web 15 is applied.

After compression, the composite core passes through a cutting device 22 and is then transferred to an accelerator device 23 before it is delivered into the line for manufacturing of absorbent articles of which the apparatus according to the disclosure is a part.

As is evident from FIG. 1, a web 15 is applied to the peripheral surface of mat-forming wheel 1 upstream of hood 5, as seen in the rotational direction of mat-forming wheel 1 illustrated by arrow A1. When such a web passes over the suction box 6, the suction forces will draw the web into the mould into abutment with the bottom thereof.

A method of using the apparatus illustrated in FIGS. 1 and 2 will now be described.

As the mat-forming wheels 1 rotates in the direction of arrows A1, the moulds 2 first passes between the hood 5 and the suction box 6. The hood 5 preferably delivers a mixture of pulp fibres and SAP-particles which is drawn into the moulds 2 by the suction forces and deposited in therein. A first core element 13 is thus formed in moulds 2. As the mat-forming wheel 2 rotates in the direction A2, the moulds 3 first successively pass between hood 7 and box 9. During this passage a thin layer of pure pulp fibres is air-laid in the moulds 3. Thereafter the moulds 3 on the mat-forming wheel 2 pass between the hood 8 and suction box 10. During this passage a layer of a mixture of pulp fibres and SAP-particles is air-laid in the moulds 3 covering the layer of pure pulp fibres. The layer of pulp and SAP-particles has a thickness of 5 mm. The concentration of SAP-particles in this layer is higher, about 50-70 wt %, than in core elements 13 air-laid in mat-forming wheel 1, in which the concentration of SAP-particles is about 10-30 wt %. The layer of nonwoven 15 nearest the bottoms of moulds 2 and the thin layers of pure pulp fibres nearest the bottoms of moulds 3 have the functions of preventing SAP-particles from obstructing and clogging the holes in the mould bottom, thereby causing an uneven distribution of air resulting in an uneven distribution of air-laid material, and from damaging the these bottom. It has surprisingly been shown that SAP-particles in a mixture of pulp fibres and SAP-particles can wear out the material in the mould bottoms. These layers also have the function of preventing SAP-particles from falling out of the core element formed in the respective mould during transport of the moulds on the respective wheel, during transfer of the first core element 12 onto the second core element 14 and during transfer of the composite core from wheel 2 to the compression device.

As is evident from FIG. 2, the moulds 3 and 4 are shallower than the core elements 13 respective 14 formed therein. After the core elements 13, 14 have been formed by air-laying in the respective moulds 2,3, the core elements 13,14 are maintained in their respective mould by suction boxes 11 respective 12 until they reach the nip between the mat-forming wheels 1,2.

The nip is preferably dimensioned so that the outsides of the core elements 13,14, i.e. the sides thereof distal from the respective mould bottom, abut each other in the nip. In other words, the nip constitutes a "marrying point" for the two core elements 13,14 in which they get together. The nip is preferably dimensioned so that normally the parts of the core elements 13,14 overlapping each other are slightly compressed in the marrying point. The suction box 11 in the first mat-forming wheel 1 ends at the marrying point. At the nip, the web 15 leaves the mat-forming wheel 1 and is applied to the peripheral surface of mat-forming wheel 2 on top of the core elements traveling on this surface. As the web 15 leaves the moulds on mat-forming wheel 1 it also draws the core element formed in the mould with it and thereby supports this core element during transfer from mat-forming wheel 1 to mat-forming wheel 2. In the example shown in FIG. 2, a part of the core element 13 is transferred so that it overlaps a part of core element 14. When this part of core element 13 during the continued rotation of wheels 1,2 leaves the nip it will now longer be subjected to suction forces maintaining it on wheel 1 but only the suction forces of suction box 12 on wheel 2. These suction forces will maintain the said part of core element 13 in abutment with the part of core element 13 which it overlaps. Due to the arrangement of the nip and the "overfilling" of moulds 2 and 3, respectively, all the overlapping points of a core element 13 will in the nip come to abutment with the outside of core element 14 while it still is maintained in mould 2 and is not until then transferred onto a core element 14. Thus an extremely controlled and accurate transfer of core elements 13,14 is accomplished. The overlapping part of core element 13 is thus subjected to suction forces from either suction box 11 on wheel 1 or suction box 12 on wheel 2 during the whole transfer.

However, the leading part of core element 13 will not be subject to suction forces after having passed the nip. If this part of the core element 13 would be left free in the air during the transfer of core element 13 onto core element 14, it would result in great losses of SAP-particles from this part due to centrifugal and gravitation forces. By providing the web 15 to control the path of the leading part of core element 13, this part is supported during the transfer and the subsequent transport traveling on wheel 2. By the provision of web 15 an overlapping transfer of a core element on one mat-forming wheel to another core element on another mat-forming wheel is enabled. Losses of SAP-particles out of core element 13 is thereby significantly reduced in relation to a transfer operation in which the core element or portions thereof are moving in free air when centrifugal and gravitation forces are not counteracted.

After the core element 13 has been transferred to wheel 2 onto the core element 14, the web 15 will also prevent SAP-particles from falling out of this core element during transport. It is to be noted that the leading part of each core element 13 moving together with wheel 2 is not subjected to the suction forces of suction box 12 but is only held against the peripheral surface of wheel 2 by the web 15. The web 15 together with the suction forces of box 12 also prevents loss of SAP-particles from the part of the core element 13 overlapping core element 14 the trailing part of core element 14 not being covered by element 13.

The transfer of the composite core element 13,14 on wheel 2 to transferring roller 17 is facilitated by an optional blowing device 20 blowing pressurised air through the bottom of moulds 4. The compressing in the compressing device 16 will be facilitated if the composite core is encapsulated in casing material from both sides during the compression. In order to accomplish this a further web 21 of casing material, preferably nonwoven, is applied to the side of core 13,14 opposite to the side to which web 15 is present before it passes between the rollers 18,19 of the compression device. Preferably, an adhesive coating is applied to web 21 by a glue applicator 29 before it is applied to the composite core 13,14.

By the apparatus described above it is thus possible to produce a core consisting of two core elements in an accurate overlapping superposed relationship to each other. It is of course also possible to produce a core in which the superposed core elements do not overlap each other. Such an apparatus makes it possible to produce cores having different sizes by varying the overlapping between the core elements.

Such an apparatus has means for controlling the produced overlap between the core elements, i.e. means for changing the synchronization of the mat-forming wheels in order to control the time at which the leading edge of a mould on one of the mat-forming wheels passes the nip in relation to when the leading edge of a mould on the other mat-forming wheel passes the nip. An easy way of controlling the overlap is to vary the start of rotation of the mat-forming wheels so that one of the mat-forming wheels starts its rotation before the other. Another way is of course to manually set an angular displacement of one wheel in relation to the other.

As stated before, such way of transferring a core element from one mat-forming wheel to the peripheral surface of another mat-forming wheel makes it possible to produce absorbent articles having different sizes without changing the moulds on the mat-forming wheels by changing overlap between the core elements merely by controlling the time when the leading edges of the moulds on the respective mat-forming wheel passes the nip. It is of course possible to place the core elements in any desired position in relation to each other on the peripheral surface of mat-forming wheel, for example with zero overlap. It is also possible to let the leading edge of the moulds on the second mat-forming wheel to pass the nip before the leading edge of the moulds on the first mat-forming wheel and dimension the moulds so that the trailing edge of the moulds on the first mat-forming wheel passes the nip after the trailing edge of the moulds on the second mat-forming wheel. By the different superposing of the core elements on each other it is also possible to change the properties of the composite core consisting of the superposed first and second core elements. Thus, the present disclosure enables a variety of composite cores to be manufactured without having to change the moulds on the mat-forming wheels.

An apparatus according to the embodiment shown enables a production of absorbent cores at a very high rate, even more than 600 cores per minute.

The apparatuses according to the described embodiments can of course be modified in several respects without leaving the scope of disclosure. For example, the thin protective layer air-laid in the moulds of the second mat-forming wheel can be substituted by a nonwoven web similar to web 15. In such a case a glue applicator applies a coating of adhesive on one of the webs, preferably web 15, before it is applied to the mat-forming wheel. The dimensions of the core elements can be different than shown and the overlapping can be made so that the trailing part of the transferred core element is only supported by the web 15 instead of leading part as in the described embodiment. Other types of casing material than nonwoven can be used and the core element on the first mat-forming wheel need not contain SAP-particles. Different fibres can be used in the different air-laying devices and the cutting device and accelerator for delivering produced cores to the production line for the manufacturing of absorbent articles can be any type of such equipment used in such production line. The disclosure shall therefore only be limited of the wording of the granted claims.

The invention claimed is:

1. A method of forming air-laid absorbent cores, the method comprising the steps of:
    forming first and second core elements by air-laying of air-entrained fibrous material to moulds on first and second mat-forming wheels, each of said mat-forming wheels having at least one mould along its peripheral surface, wherein each mould on the first and second mat-forming wheels has a leading edge and a trailing edge;
    the method further comprising:
    applying a sheet of casing material to the peripheral surface of the first mat-forming wheel before air-laying of a mixture of air-entrained fibrous material and discrete particles in the mould,
    transferring said sheet of casing material to the periphery of the second mat-forming wheel after having passed a nip between the first and second mat-forming wheel, whereby the first core element is transferred together with the sheet onto the periphery of the second mat-forming wheel,
    controlling the time at which the leading edge of a mould on one of the mat-forming wheels passes the nip in relation to when the leading edge of a mould on the other mat-forming wheel passes the nip in dependence of the desired relative position of the first and second core elements on the peripheral surface of the second mat-forming wheel, and
    transferring the core elements from the second mat-forming wheel to other components in a production line for the manufacturing of sanitary absorbent articles.

2. The method according to claim 1, wherein the leading edge of the moulds on the first mat-forming wheel passes the nip formed between the first and second mat-forming wheels before the leading edge of the moulds on the second mat-forming wheel.

3. The method according to claim 2, wherein the trailing edge of the moulds on the first mat-forming wheel passes the nip formed between the first and second mat-forming wheels before the trailing edge of the moulds on the second mat-forming wheel.

4. The method according claim 2, wherein the leading edge and trailing edge of the moulds on the first mat-forming wheel pass the nip formed between the first and second mat-forming wheels before the leading edge of the moulds on the second mat-forming wheel.

5. The method according to claim 2, wherein a mixture of air-entrained fibrous material and discrete particles is supplied to both the first and second mat-forming wheels and a sheet of nonwoven is applied to the peripheral surface of both the first and second mat-forming wheels.

6. The method according to claim 2, wherein a sheet of casing material is applied to each of the first and second mat-forming wheels and an adhesive coating is applied on at least one of said sheets on the side thereof distal from the bottom of the moulds.

7. The method according to claim 1, wherein the nip between the first and second mat-forming wheels is such that sides of the first and second core elements distal from the respective mould bottoms will abut each other in the nip.

8. An apparatus for forming air-laid absorbent cores, the apparatus comprising:
first and second mat-forming wheels, each of the mat-forming wheels having a series of moulds along its peripheral surface,
air-laying means for supplying air-entrained fibrous material to the moulds on each mat-forming wheel,
suction means maintaining the formed core elements in the respective moulds during a part of the path of the moulds on the respective mat-forming wheel and
means for transferring a core element on the first mat-forming wheel onto the peripheral surface of the second mat-forming wheel while the core element on the second mat-forming wheel still is maintained in its mould,
the apparatus further comprising:
means for applying a sheet of casing material on the peripheral surface of the first mat-forming wheel, whereby suction means inside the first mat-forming wheel will draw the material in the sheet to abutment against the bottom of a mould passing said suction means,
means for guiding said sheet of casing material onto the periphery of the second mat-forming wheel after having passed a nip between the first and second mat-forming wheels, and
means for changing the synchronization of the mat-forming wheels in order to control the time at which the leading edge of a mould on one of the mat-forming wheels passes the nip in relation to when the leading edge of a mould on the other mat-forming wheel passes the nip.

9. The apparatus according to claim 8, wherein at least the air-laying means associated with the second mat-forming wheel comprises means for supplying a mixture of air-entrained fibrous material and discrete particles and means for applying a protective layer to the bottom of each mould of the second mat-forming wheel.

10. The apparatus according to claim 9, wherein both the first and second mat-forming wheels include means for supplying a mixture of air-entrained fibrous material and discrete particles and means for applying a sheet of nonwoven to the peripheral surface of each mat-forming wheel.

11. The apparatus according to claim 9, wherein the moulds of the mat-forming wheels have different sizes, at least in the circumferential direction of the mat-forming wheels, and the moulds on the first mat-forming wheel are larger than the moulds on the second mat-forming wheel.

12. The apparatus according to claim 8, wherein the nip between the first and second mat-forming wheels is such that sides of the first and second core elements distal from the respective mould bottoms will abut each other in the nip.

* * * * *